US00PP11465P

United States Patent [19]

van Rijn

[11] Patent Number: Plant 11,465

[45] Date of Patent: Jul. 25, 2000

[54] ANTHURIUM PLANT NAMED 'SASKIA'

[75] Inventor: Leonardus van Rijn, Schipluiden, Netherlands

[73] Assignee: Rijnplant B.V., Schipluiden, Netherlands

[21] Appl. No.: 09/177,591

[22] Filed: Oct. 22, 1998

[51] Int. Cl.[7] ..... A01H 5/00

[52] U.S. Cl. ..... Plt./365

[58] Field of Search ..... Plt./365, 369

*Primary Examiner*—Howard J. Locker

*Assistant Examiner*—Kent L. Bell

*Attorney, Agent, or Firm*—C. A. Whealy

[57] ABSTRACT

A distinct cultivar of Anthurium plant named 'Saskia', characterized by its upright, outwardly arching and very freely clumping growth habit; strong rooting system; durable dark green leaves that are oblong to ovate in shape; numerous inflorescences that are positioned upright and above the foliage on strong and erect scapes; durable fire red spathes; year-round continuous flowering; and good post-production longevity.

2 Drawing Sheets

BACKGROUND OF THE INVENTION

The present invention relates to a new and distinct cultivar of Anthurium plant, botanically known as *Anthurium andreanum,* and hereinafter referred to by the cultivar name 'Saskia'.

The new Anthurium is a product of a planned breeding program conducted by the Inventor in Schipluiden, The Netherlands. The objective of the program is to create new Anthurium cultivars that have a freely clumping growth habit, strong plant growth, attractive spathe color, numerous inflorescences and leaves, and good post-production longevity.

The new Anthurium originated from a cross by the Inventor in August, 1991 of the Inventor's proprietary *Anthurium andreanum* selection code number 90-3 as the female, or seed, parent with the Inventor's proprietary *Anthurium andreanum* selection code number 90-6 as the male, or pollen, parent. The cultivar 'Saskia' was discovered and selected by the Inventor as a plant within the progeny of the stated cross in a controlled environment in Schipluiden, The Netherlands in June, 1993.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Saskia'. These characteristics in combination distinguish 'Saskia' as a new and distinct cultivar:

1. Upright, outwardly arching and very freely clumping growth habit.

2. Strong rooting system.

3. Durable dark green leaves that are oblong to ovate in shape.

4. Numerous inflorescences that are positioned upright and above the foliage on strong and erect scapes.

5. Durable fire red spathes.

6. Year-round continuous flowering.

7. Good post-production longevity.

The new Anthurium can be compared to the female parent, the Inventor's propietary selection code number 90-3. In side-by-side comparisons conducted by the Inventor in Schipluiden, The Netherlands, plants of the new Anthurium differ from plants of selection code number 90-3 in the following characteristics:

1. Plants of the new Anthurium are more compact than plants of the selection code number 90-3.

2. Plants of the new Anthurium have smaller and more durable leaves than plants of the selection code number 90-3.

3. Plants of the new Anthurium have smaller and more durable spathes than plants of the selection code number 90-3.

The new Anthurium can be compared to the male parent, the Inventor's proprietary selection code number 90-6. In side-by-side comparisons conducted by the Inventor in Schipluiden, The Netherlands, plants of the new Anthurium differ from plants of selection code number 90-6 in the following characteristics:

1. Plants of the new Anthurium have red-colored spathes whereas plants of the selection code number 90-6 have pink-colored spathes.

2. Plants of the new Anthurium have thinner, darker green and more durable leaves than plants of the selection code number 90-6.

3. Plants of the new Anthurium have more durable spathes than plants of the selection code number 90-6.

Compared to plants of the sibling cultivar 'Cora', disclosed in U.S. Plant Patent application Ser. No. 09/177,290, plants of the new Anthurium have lighter red-colored spathes. Compared to plants of the sibling cultivar 'Claudia', disclosed in U.S. Plant Patent application Ser. No. 09/177,594, plants of the new Anthurium are shorter and have smaller leaves and spathes.

The new Anthurium can be compared to the nonpatented Anthurium cultivar 'Lisette'. In side-by-side comparisons conducted by the Inventor in Schipluiden, The Netherlands, plants of the new Anthurium differ from plants of the cultivar 'Lisette' in the following characteristics:

1. Plants of the new Anthurium have thicker, rougher, lighter green and are less pointed than leaves than plants of the cultivar 'Lisette'.

2. Plants of the new Anthurium have red-colored spathes whereas plants of the cultivar 'Lisette' have pink-colored spathes.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type.

The photograph on the first sheet comprises a top perspective view of a typical potted plant of the cultivar 'Saskia'.

The photograph on the second sheet comprises a close-up view of a typical spathe and spadix of the cultivar 'Saskia'. Leaf, spathe and spadix colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants grown in Schipluiden, The Netherlands, in a glass greenhouse with an average day temperature 25° C. and an average night temperature of 19° C.

Botanical classification: *Anthurium andreanum* cultivar 'Saskia'.

Parentage:

*Female parent*.—Inventor's proprietary *Anthurium andreanum* selection code number 90-3.

*Male parent*.—Inventor's proprietary Anthurium andreanum selection code number 90-6.

Propagation:

*Method*.—Typically by tissue culture.

*Time to initiate roots*.—About 70 or 84 days at 24° C. or 21° C., respectively.

*Rooting habit*.—Numerous and very strong fleshy roots.

Plant description:

*Plant shape*.—Upright, inverted triangle, symmetrical.

*Growth habit*.—Erect when young, becoming outwardly arching as leaves develop. Freely clumping, bushy and dense. Appropriate for 17 to 35-cm containers.

*Plant height*.—About 47.5 cm from soil level to apex of spathes.

*Plant vigor*.—High.

*Growth rate*.—Moderate to rapid.

*Crop time*.—About 10 months are usually required from planting of young plants to finished plants in 17-cm containers.

*Foliage description*.—Quantity; Usually about 25 leaves per contianer. Length: About 21 cm. Width: About 15 cm. Shape: Oblong to ovate. Apex: Apiculate. Base: Auriculate to cordate; lobes not overlapping. Margin: Entire. Texture: Smooth, glabrous, leathery. Color: Young leaves, upper surface: 178A with green tones. Young leaves, lower surface: 178A with green tones. Mature leaves, upper surface: Between 139A and 147A. Mature leaves, lower surface: Darker than 144A. Petiole: Length: About 31 cm. Color: Darker than 144A. Geniculum length: About 4,5 cm.

Inflorescence description:

*Inlorescence arrangement*.—Spathe with spadix held above the foliage. Flowering structures arise from leaf axils. Freely flowering; continuous flowering year-round; typically five to nine inflorescences per plant. Not fragrant.

*Inflorescence longevity*.—Inflorescences last about six weeks under winter conditions and up to three months under summer conditions; persistent.

*Flowers*.—Quantity per spadix: Numerous, about 150. Shape: Rounded. Diameter: About 1 mm, maximum.

*Spathe*.—Length: About 7 cm. Width: About 6 cm. Height above foliage: About 8.5 cm. Shape: Deltoid. Apex: Apiculate to mucronate. Base: Auriculate to cordate; lobes not overlapping. Margin: Entire. Texture: Leathery, glabrous, very slight blistering, shiny. Color: When opening: 45A. Front surface: 46B. Back surface: 45C to 45D. After senescence: 46A.

*Spadix*.—Length: About 5.5 cm. Diameter: About 1 cm. Shape: Columnar. Cross section: Rounded. Longitudinal axis: Very weakly recurved. Color: Base: Creamy white with orange coloration, 33C. Midsection: Close to 39B to 33C. Apex: 41C. Color, after senescence: 33B.

*Scape*.—Length: About 40 cm. Aspect: Strong and erect. Color: 144A, darker green with anthocyanin towards apex.

*Reproduction organs*.—Androecium: Pollen color: Creamy white, 159B. Gynoecium: Stigma shape: Ovoid.

Disease resistance: Plants of the new Anthurium have not been shown to be resistant to diseases common to Anthurium.

Seed development: Seed development on plants of the new Anthurium has not been observed.

It is claimed:

1. A new and distinct cultivar of Anthurium plant named 'Saskia', as illustrated and described.

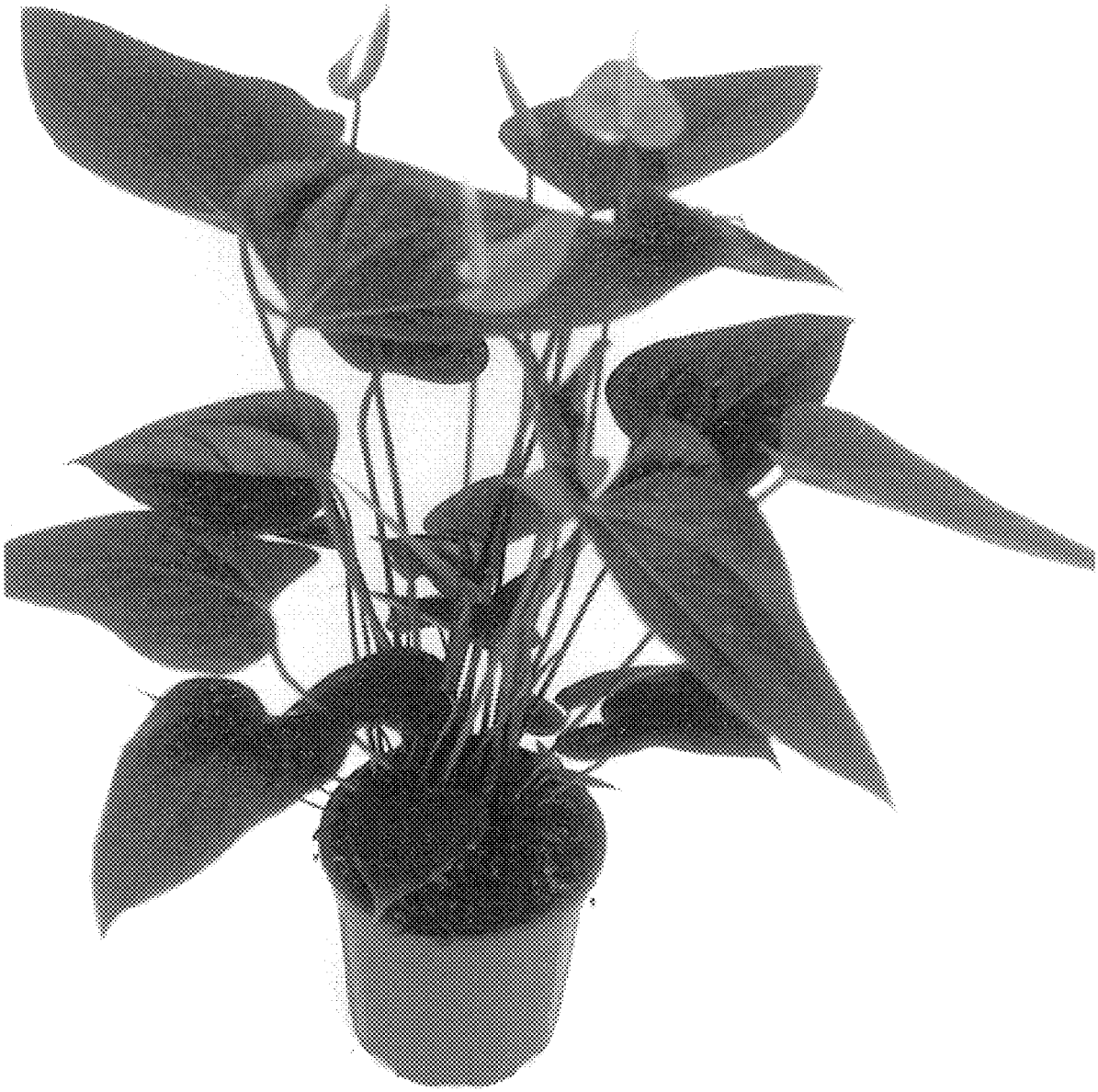

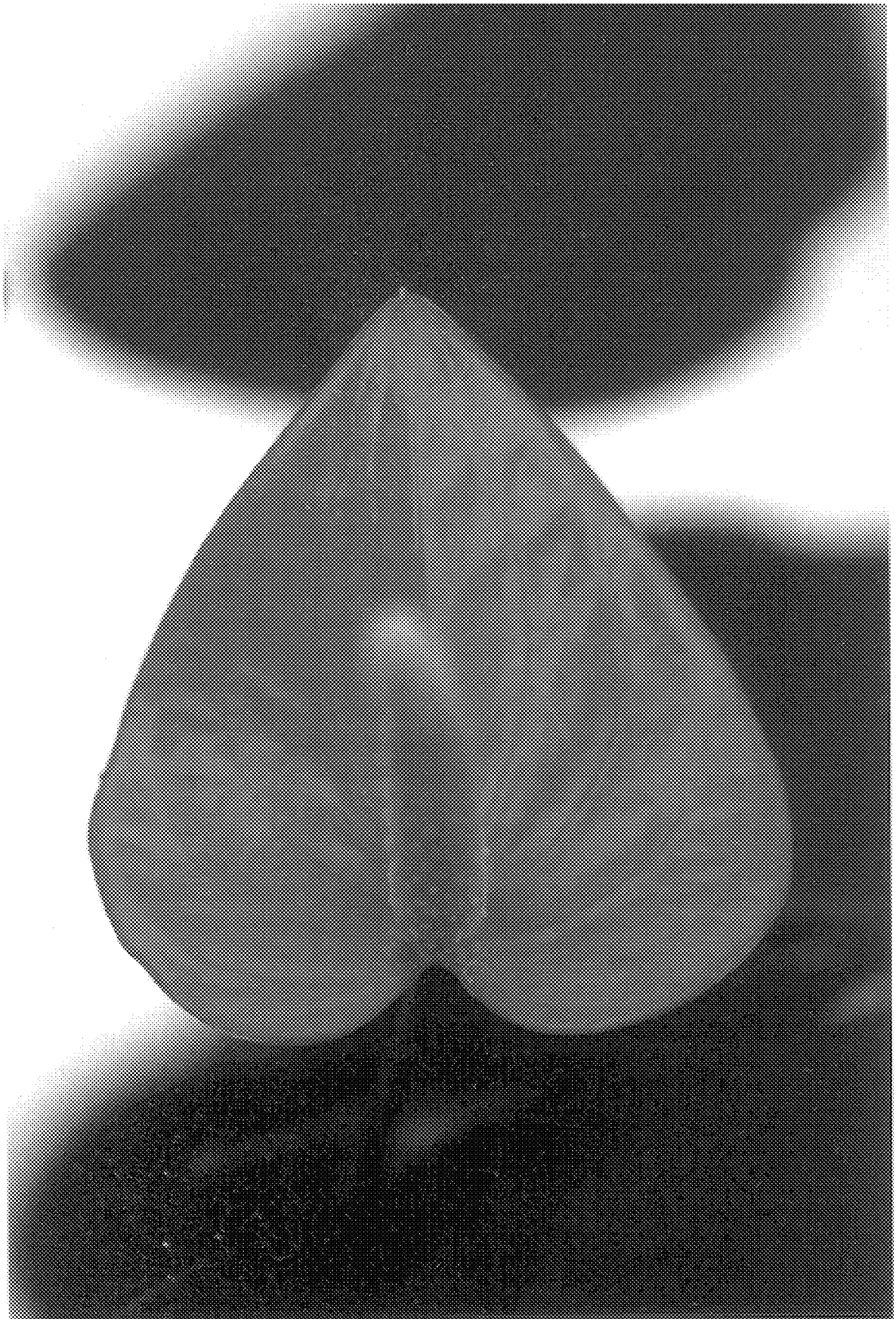

* * * * *